(12) United States Patent
Fleissner et al.

(10) Patent No.: US 6,706,727 B1
(45) Date of Patent: Mar. 16, 2004

(54) MACROLIDES

(75) Inventors: Gerhard Fleissner, Kufstein (AT);
Helmut Häcker, Kiefersfelden (DE);
Ernst Küsters, Eschbach (DE);
Gerhard Penn, Oberwil (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/276,622
(22) PCT Filed: May 21, 2001
(86) PCT No.: PCT/EP01/05836
§ 371 (c)(1), (2), (4) Date: Nov. 18, 2002
(87) PCT Pub. No.: WO01/90110
PCT Pub. Date: Nov. 29, 2001

(51) Int. Cl.$^7$ .................... C07D 498/18; A61K 31/436; A61P 37/06
(52) U.S. Cl. ....................... 514/291; 540/456
(58) Field of Search ............ 540/456; 514/291

(56) References Cited

FOREIGN PATENT DOCUMENTS

EP       0 427 680 A       5/1991

OTHER PUBLICATIONS

Junker B., et al., "Secondary metabolite scale–up to minimize homolog impurity levels," Boitechnology and Bioengineering, vol. 59(5), pp. 595–604 (1998).
Hersperger R., et al., "Ascomycin Derivatives and Their Use as Immunosuppressive Agents," Drugs of the Future, Barcelona, ES, vol. 25(3), pp. 269–277 (2000).

*Primary Examiner*—Bruck Kifle
(74) *Attorney, Agent, or Firm*—D. Gabrielle Brouillette

(57) ABSTRACT

The composition of formula I

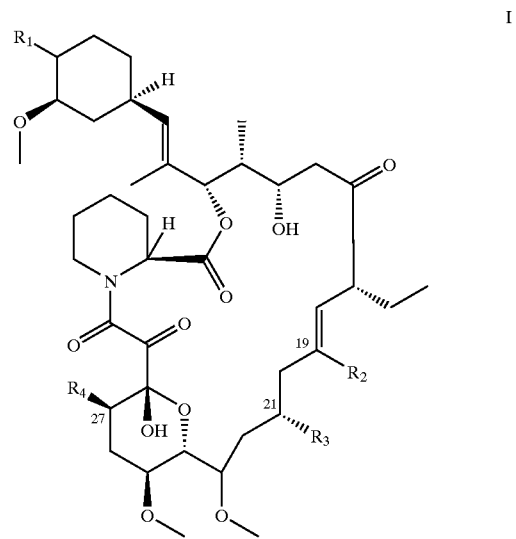

wherein the substituents have various significances, whereby one of $R_2$ to $R_4$ is ethyl. They can be prepared by fermentation, or by replacement of hydroxy with chloro under simultaneous or concomitant epimerization. They are indicated for use as pharmaceuticals in the prevention or treatment of inflammatory conditions and of conditions requiring immunosuppression, optionally in combination or association with further pharmaceutically active and compatible agents, e.g. macrolactam macrolides such as pimecrolimus.

7 Claims, No Drawings

MACROLIDES

The invention relates to macrolides, particularly to macrolactam macrolides. It concerns the compounds of formula I

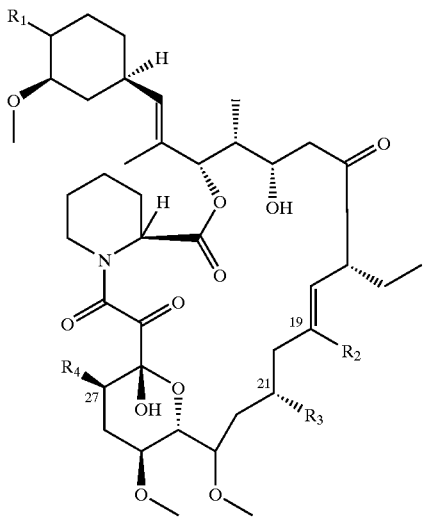

wherein either
  $R_1$ is hydroxy in the β-configuration; and
  $R_2$ is methyl and
  one of $R_3$ and $R_4$ is ethyl and the other is methyl; or
  $R_1$ is chloro in the α-configuration; and
  one of $R_2$, $R_3$ and $R_4$ is ethyl and the others are methyl;
in free form and, where such forms exist, in salt form, hereinafter briefly named "the compound of the invention".

When $R_1$ in formula I is in the α-configuration it is above, and when it is in the β-configuration it is below, the plane of the paper. $R_1$ preferably is chloro in the α-configuration. $R_3$ or $R_4$, particularly $R_3$, preferably is ethyl.

The compounds of the invention are hereinafter briefly named as follows:
  when $R_1$ is hydroxy and
    $R_3$ is ethyl: 21-ethyl-ascomycin; or
    $R_4$ is ethyl: 27-ethyl-ascomycin;
  when $R_1$ is chloro and
    $R_2$ is ethyl: 19-ethyl-ASM; or
    $R_3$ is ethyl: 21-ethyl-ASM; or
    $R_4$ is ethyl: 27-ethyl-ASM;
i.e. they are, respectively:

(1R,9S,12S,13R,14S,17R,18E,21S,23S,24R,25S,27R)-12-[(1E-2-[(1R,3R,4R)-4hydroxy-3-methoxycyclohexyl]-1-methylvinyl]-17,21-diethyl-1,14-dihydroxy-23,25-dimethoxy-13,19,27-trimethyl-11,28-dioxa-4-azatricyclo-[22.3.1.0$^{4,9}$]octacos-18-ene-2,3,10,16-tetrone;
(1R,9S,12S,13R,14S,17R,18E,21S,23S,24R,25S,27R)-12-[(1E-2-[(1R,3R,4)-4-hydroxy-3-methoxycyclohexyl]-1-methylvinyl]-17,27-diethyl-1,14-dihydroxy-23,25-dimethoxy-13,19,21-trimethyl-11,28-dioxa-4-azatricyclo-[22.3.1.0$^{4,9}$]octacos-18-ene-2,3,10,16-tetrone;
(1R,9S,12S,13R,14S,17R,18E,21S,23S,24R,25S,27R)-12-[(1E-2-[(1R,3R,4S)-4-chloro-3-methoxycyclohexyl]-1-methylvinyl]-17,19-diethyl-1,14-dihydroxy-23,25-dimethoxy-13,21,27-trimethyl-11,28-dioxa-4-azatricyclo-[22.3.1.0$^{4,9}$]octacos-18-ene-2,3,10,16-tetrone;
(1R,9S,12S,13R,14S,17R,18E,21S,23S,24R,25S,27R)-12-[(1E-2-[(1R,3R,4S)-4-chloro-3-methoxycyclohexyl]-1-methylvinyl]-17,21-diethyl-1,14-dihydroxy-23,25-dimethoxy-13,19,27-trimethyl-11,28-dioxa-4-azatricyclo-[22.3.1.0$^{4,9}$]octacos-18-ene-2,3,10,16-tetrone; and
(1R,9S,12S,13R,14S,17R,18E,21S,23S,24R,25S,27R)-12-[(1E-2-[(1R,3R,4S)-4-chloro-3-methoxycyclohexyl]-1-methylvinyl]-17,27-diethyl-1,14-dihydroxy-23,25-dimethoxy-13,19,21-trimethyl-11,28-dioxa-4-azatricyclo-[22.3.1.0$^{4,9}$]octacos-18-ene-2,3,10,16-tetrone.

21-Ethyl-ascomycin and 27-ethyl-ascomycin are higher homologues of ascomycin. 19-Ethyl-ASM, 21-ethyl-ASM and 27-ethyl-ASM are higher homologues of pimecrolimus (ASM) (33-epichloro-33-desoxy-ascomycin).

The compounds of the invention can be prepared by a process comprising
  a) for the preparation of the compounds of formula I as defined above wherein $R_1$ is hydroxy in the β-configuration,
    cultivating an appropriate microorganism and isolating from the resultant culture medium the corresponding compounds of formula I wherein $R_1$ is hydroxy in the β-configuration; or
  b) for the preparation of the compounds of formula I as defined above wherein $R_1$ is chloro in the α-configuration,
    replacing under epimerization hydroxy with chloro in a corresponding compound of formula I wherein $R_1$ is hydroxy in the β-configuration,
and recovering the resultant compounds in free form or, where such forms exist, in salt form The process of the invention is effected in conventional manner.

In variant a) any ascomycin-producing microorganism strain may be used which produces higher homologues of ascomycin, e.g. as impurities, preferably a Streptomyces hygroscopicus strain. Such strains are known and available from public depositories. Preferably, strains are used which produce significant amounts of higher homologues of ascomycin, or cultivation conditions are chosen which allow preparation of enhanced amounts of higher homologues of ascomycin. Such strains are known and readily accessible, such as *Streptomyces hygroscopicus* subsp. *ascomyceticus* (e.g. ATCC 14891, ATCC 53855, ATCC 55087, ATCC 55276, ATCC 55558, DSM 5085), *Streptomyces tsukubaensis* No. 9993 (FERM BP-927), *Streptomyces hygroscopicus* subsp. *yakushimaensis* No. 7238 (FERM BP-928, NRRL 18488); or natural or artificial mutants thereof, and cultivation conditions for enhanced higher homologues production are known or can readily be determined in conventional manner therefrom Conveniently, appropriate mutant strains may be created exhibiting enhanced higher homologues production, or selected, in conventional manner, or culture may be effected under modified conditions, such as with increased concentration of the C4 precursor sodium butyrate in the culture medium.

Variant b) is a substitution reaction under simultaneous or concomittant epimerization. It is effected e.g. as described in EP 427680. It preferably is effected in an inert solvent such as tetrahydrofurane or toluene. Preferably the reaction is effected with tetrachloromethane or N-chloro-succmimide in the presence of triphenylphosphine, conveniently in an alkaline medium such as collidine.

The resultant compounds of the invention may be isolated from the cultivation or reaction mixture and purified in accordance with known methods. However, it has been found that, surprisingly, use of a chiral stationary phase such as Kromasil® during chromatographic purification may greatly facilitate isolation of, in particular, the compounds of the invention wherein $R_1$ is chloro.

The starting materials and intermediate compounds are either known or can be prepared according to known methods or analogously to known methods or analogously as described in the Examples.

The following Examples illustrate the invention. They are not limitative. All temperatures are in degrees Celsius. The compounds are in free form unless specified otherwise. The following abbreviations are used:

| HPLC | high pressure liquid chromatography |
|------|-------------------------------------|
| I.D. | internal diameter |
| THF  | tetrahydrofurane |
| tlc  | thin layer chromatography |
| %    | percent w/w |

EXAMPLE 1

21-Ethyl-ascomycin and 27-ethyl-ascomycin

[Process Variant a)]

a)

Crude ascomycin is prepared on a semi-industrial (kg) scale by fermentation of a Streptomyces strain (ATCC 14891), as described in Example 4 of EP 184162, and partially purified by countercurrent extraction (Res.Discl. 402 [October 1997] 725–726). A crude product is obtained, containing about 35% ascomycin, 15% 21-ethyl-ascomycin and 10% 27-ethyl-ascomycin. This material is fer purified in a silica gel filtration step using isopropyl acetate/n-heptane 7/3 (v/v) as an eluant to remove ascomycin. The resultant further crude product obtained contains about 25% 21-ethyl-ascomycin and 15% 27-ethyl-ascomycin.

b)

1 g crude 21-ethyl-ascomycin from a) above is dissolved in 3.5 ml of isopropyl acetate/heptane 7/3 (v/v), and the feed solution is injected on a preparative column (36 cm×5 cm I.D.) containing 300 g silicagel [Kromasil® 100-5 SIL (Eka Nobel)] as stationary phase. The mixture is eluted with isopropyl acetate/heptane 7/3 (v/v) as mobile phase with a flow rate of 100 ml/min at room temperature. UV-detection occurs at 245 nm. The ascomycin derivatives elute after 34.5 min and are fractionated in intervals of 1.1 min. 21-Ethyl-ascomycin is collected in fractions 13–28. The pooled fractions are collected and evaporated to dryness at 40° under vacuum. Thirteen preparative runs yield more than 1 g of title compound 21-ethyl-ascomycin:

FAB-MS: fragments in decreasing order: 812 [M+Li]⁻, 602, 794, 425;

2D-¹H-NMR: 21-ethyl=1.21 ppm, 1.50 ppm (methylene) and 0.87 ppm (methyl).

c)

1 g crude 27-ethyl-ascomycin from a) above is treated as described under b) above, except that co-eluting fractions 1–7 are collected. The pooled fractions are collected and evaporated to dryness at 40° under vacuum 379 mg of the resultant residue are dissolved in 30 ml of n-hexane/ethanol/methanol 90/5/5 (v/v/v), and the feed solution is injected on a preparative column (40 cm×10 cm I.D.) containing 2.0 kg amylose tris(3,5-dimethylphenylcarbamate) (coated on silicagel) (Chiralpak-AD®). Elution is effected with n-hexane/ethanol/methanol 90/5/5 (v/v/v) as mobile phase with a flow rate of 150 ml/min at room temperature. UV-detection occurs at 210 nm. 27-Ethyl-ascomycin elutes between 60 and 80 min. The 27-ethyl-ascomycin containing fractions are collected and evaporated to dryness at 40° under vacuum, yielding 120 mg of title compound 27-ethyl-ascomycin:

FAB-MS: fragments in decreasing order: 828.6 [M+Na]⁺, 508.3, 423.0, 563.6;

2D-¹H-NMR: 27-ethyl=1.59 ppm, 1.19 ppm (methylene) and 0.92 ppm (methyl).

EXAMPLE 2

19-Ethyl-ASM

[Process Variant b)]

a)

ASM is prepared on a semi-industrial (kg) scale using the procedure described in EP 427680, Example 66a, starting from crude ascomycin, and submitted to chromatographic purification over silicagel at 40–45° using heptane/tert-butyl methyl ether (water-saturated)/isopropanol 200/50/8 (v/v) as an eluant. A side fraction from the chromatographic run is obtained having a content of 56% of crude 19-ethyl-ASM.

b)

Preparative tlc is effected on 17 mg crude product from a) above, dissolved in 1 ml of methylene chloride and charged on a tlc plate (Merck 5715, 20×20 cm I.D.). The chromatogram is developed using a mixture of pentane/isopropanol 9/1 (v/v) as mobile phase within 18 cm distance. The zone containing 19-ethyl-ASM (Rf=0.35) is removed from the tlc plate and washed with 2 ml of pentane. The product is extracted with 5 ml of acetonitrile and dried at 60° under vacuum, yielding 4.4 mg title compound with a purity of ≧90%:

FAB-MS: fragments in decreasing order. 830 [M+Li]⁺, 602, 313, 578, 788;

2D-¹H-NMR: 19-ethyl=2.17 ppm, 1.82 ppm (methylene) and 0.98 ppm (methyl)].

EXAMPLE 3

19-Ethyl-ASM

[Process Variant b)]

The title compound is obtained analogously as described in Example 4 hereunder, starting from 19-ethyl-ascomycin, i.e. (1R,9S,12S,13R,14S,17R,18E,21S,23S,24R,25S,27R)-12-[(1E-2-[(1R,3R,4R)-4-hydroxy-3-methoxycyclohexyl]-1-methylvinyl]-17,19-diethyl-1,14-dihydroxy-23,25-dimethoxy-13,21,27-trimethyl-11,28-dioxa-4-azatricyclo-[22.3.1.0⁴,⁹]octacos-18-ene-2,3,10,16-tetrone (B. Junker et al., *Biotechnol. Bioeng.* 59 [1998] 595–604):

FAB-MS: fragments in decreasing order: 830 [M+Li]⁺, 602, 313, 578, 788;

2D-¹H-NMR: 19-ethyl=2.17 ppm, 1.82 ppm (methylene) and 0.98 ppm (methyl)].

EXAMPLE 4

21-Ethyl-ASM

[Process Variant b)]

a)

0.733 g 21-ethyl-ascomycin [see Example 1b) above] is dissolved twice in 2.5 ml of toluene and evaporated at 50° under vacuum. In a separate 25 ml flask 0.298 g triphenylphosphine is dissolved in 4.7 ml of tetrahydrofurane, 0.152 g N-chloro-succinimide is added and the suspension is stirred for 30 min at room temperature. To that suspension 0.202 ml of s-collidin is added, followed by the solution of the above dried 21-ethyl-ascomycin in 3.9 ml of tetrahydrofurane. The solution is finally heated up to 50° for 1.5 h and then cooled down to room temperature. 16.6 ml of cyclohexane are added and the organic phase is extracted with 0.18 g citric acid in a mixture of 3.5 ml of water and 3.5 ml of methanol. The organic phase is again extracted twice with 7 ml of methanol/water 1/1 (v/v) and the combined water phase is re-extracted with 10 ml of cyclohexane. The solvent is evaporated at 50° yielding 0.79 g crude 21-ethyl-ASM.

b)

0.1 g crude product from a) above is dissolved in 1.0 ml of ethanol and the feed solution is injected on a preparative column (25 cm×2 cm I.D.) containing 55 g reversed-phase silicagel [Kromasil® RP-18 (5 µm)] as stationary phase. The product is eluted with 70% solvent B [solvent A=water/ phosphoric acid 1000/1 (v/v); solvent B=acetonitrile/tert-butyl methyl ether 825/175 (v/v)] as mobile phase with a flow rate of 15 ml/min at 60°. UV-detection occurs at 210 nm. 21-Ethyl-ASM elutes at between 11.5 min and 12.0 min. The organic solvents of the product fraction are evaporated at 50° under vacuum and the remaining water phase is extracted twice with 15 ml of methylene chloride each. Methylene chloride is finally evaporated at 50° under vacuum, yielding 30 mg title compound:

FAB-MS: fragments in decreasing order: 830 [M+Li]$^+$, 397, 149;

2D-$^1$H-NMR: 21-ethyl=1.30 ppm, 1.20 ppm (methylene) and 0.90 ppm (methyl).

EXAMPLE 5

27-Ethyl-ASM

[Process Variant b)]

a)

135 mg 27-ethyl-ascomycin [see Example 1c) above] is dissolved in 1.4 ml of toluene and the solvent is distilled off at 60°/80–20 mbar. The residue is dissolved in 0.36 ml of THF (<0.01% H$_2$O). In a separate flask 41.4 mg triphenylphosphine and 21.1 mg N-chloro-succinimide in 0.4 ml of TBF are stirred at 20° for 0.5 hours, then 27.4 mg s-collidine is added, followed by the addition of the solution of 27-ethyl-ascomycin, which is rinsed with 30 µl THF. The suspension is heated to 50–53° for 2 hours and an HPLC-analysis is made. When the reaction is completed, the mixture is cooled to 30° and 1.25 ml cyclohexane is added, followed by 26.1 mg anhydrous citric acid dissolved in 0.53 ml water/methanol 1/1 (v/v). The upper layer is separated and washed with 2×0.3 ml water/methanol 1/1 (v/v). The aqueous layers are extracted with 2×0.3 ml cyclohexane. The combined organic phases are evaporated at 50°/80–20 mbar to yield 109 mg crude 27-ethyl-ASM (brown resin).

b)

0.052 g crude product from a) above are dissolved in 1.0 ml acetonitrile, and the feed solution is injected on a preparative column (25 cm×2 cm I.D.) containing 55 g reversed-phase silicagel [Kromasil® RP-18 (5 µm)] as stationary phase. The product is eluted with acetonitrile/water/tert-butyl methyl ether 700/300/50 (v/v/v) as mobile phase with a flow rate of 15 ml/min at 60°. UV-detection occurs at 210 nm. 27-Ethyl-ASM elutes at between 15.0 min and 25.0 min. The organic solvents of the product fraction are evaporated, yielding 12.4 mg title compound:

FAB-MS: fragments in decreasing order: 846.7 [M+Na]$^+$, 810.5, 433;

2D-$^1$H-NMR: 27-ethyl=1.20 ppm, 1.20 ppm (methylene) and 0.90 ppm (methyl).

The compounds of the invention have initially been detected as impurities during scaling-up in the preparation of, respectively, ascomycin and ASM. Following on their identification and characterization it was found that, unexpectedly, they possess significant, surprisingly strong pharmacological activity. They are therefore indicated for use as pharmaceuticals. In particular, they possess immunosuppressant and antihyperproliferative, and antiinflammatory activity.

The antiinflammatory activity may e.g. be determined in the following test method:

Oxazolone-induced allergic contact dermatitis (mouse)

[F. M. Dietrich and R. Hess, *Int. Arch. Allergy* 38 (1970) 246–259]:

The compounds of the invention inhibit inflammatory swelling by about 10% to about 50% upon a single topical application as a 0.1 mM solution, and by about 40% to about 60% as a 1 mM solution.

The immunosuppressant and antihyperproliferative activity may e.g. be determined in the following test method:

Allegen-mediated stimulation of a helper T-cell clone by dendritic cells

[*Br. J. Dermatol.* 141 (1999) 264–273]:

The compounds of the invention inhibit stimulation (IC$_{50}$) at a dosage of from about 0.1 nM to about 10 nM, particularly from about 0.1 nM to about 1 nM as regards the ascomycin homologs, and from about 1 nM to about 10 nM as regards the ASM homologs.

This activity is further evidenced in additional testing with the above helper T-cell clone and monocyte-derived dendritic cells:

The CD4$^+$ antigen-specific human helper T-cell clone (TCC) is established by limiting dilution culture (Van Reijsen T. C. et al, *J. Allergy Clin. Immunol.* 90 [1992] 184–193). The TCC recognizes a peptide derived from the major allergen Der p1 of the house dust mite *Dermatophagoides pteronyssinus* (Dpt) in association with the MHC class II restriction molecule HLA-DPw4 (Baselmnns P. J. et al., *Human Immunol.* 61 [2000] 789–798). To obtain sufficient cell numbers for assay purposes, the TCC is expanded in vitro by activation with immobilized anti-CD3 monoclonal antibody (Leu4, Becton Dickinson, San Jose, Calif., USA) and culture in complete medium supplemented with rIL-2 and rhIL-4 (50 U/ml each) (Van Reijsen et al., supra).

Human monocyte-derived dendritic cells (M-DC) are generated from purified monocytes by culturing in RPMI 1640 culture medium at a cell density of 7×10$^5$ cells/ml. The culture medium is supplemented with 15% FCS and rh-GM-CSF (300 U/ml) and rh-IL-4 (100 U/ml). At day 7 of culture, 90–95% of the cells express the phenotype of M-DC as verified by flow cytometry and they are used for antigen-specific stimulation of the TCC, which is used at least 14 days after the last challenge by antigen or anti-CD3 mAb to ensure a resting state of the cells. For antigen-specific stimulation, the M-DC are incubated overnight (at least 12 h) in culture medium containing 50 µ/ml of the extract of Dpt (ARTU Biologicals NV, Lelystad, The Netherlands). The content of the major allergen Der p1 used is about 18.5 µg/mg of Dpt extract. The M-DC are washed twice and 50 µl aliquots of the final number of M-DC are added to 5×10$^4$ T-cells per well in 100 µl medium, giving a M-DC/T-cell ratio of 1/50. Immediately thereafter, 50 µl aliquots of a four-fold final concentration of test compound are added. Each sample is tested in quadruplicate. The test compound is dissolved in ethanol to provide a stock solution of 1 mM and diluted 1/1000 in the complete culture medium that is also used to prepare the final test compound dilution. T-cell proliferation is determined by pulsing with 1 μCi/20 μl/well of (methyl-)³H-thymidine (Amersham, U.K) during the final 16 hours of a 4 day culture period.

The following $IC_{50}$ values have been obtained:

TABLE

| Compound | $IC_{50}$ (nM) |
|---|---|
| 21-ethyl-ascomycin | 0.33 |
| 27-ethyl-ascomycin | 0.88 |
| 19-ethyl-ASM | 6.8 |
| 21-ethyl-ASM | 1.6 |
| 27-ethyl-ASM | 4.6 |

The compounds of the invention in free form and where such forms exist in pharmaceutically acceptable salt form are therefore indicated as antiinflamatory agents and immunosuppressant and antiproliferative agents for use in the prevention and treatment of inflammatory conditions and of conditions requiring immunosuppression, such as:

a) the treatment of inflammatory and hyperproliferative skin diseases, such as psoriasis, atopic dermatitis, contact dermatitis and further eczematous dermatoses, seborrhoeic dermatitis, *Lichen planus,* Pemphigus, bullous Pemphigoid, Epidermolysis bullosa, vasculitides, erythemas, cutaneous eosinophillas, *Lupus erythematosus* and acne;
b) the prevention and treatment of allergic diseases such as extrinsic asthma, rhinitis, conjunctivitis, atopic eczema, urticaria/angioedema, food/drug allergy and anaphylaxis;
c) the prevention and treatment of:
   resistance in situations of organ or tissue transplantation, e.g. of heart, kidney, liver, bone marrow and skin,
   graft-versus-host disease, such as following bone marrow grafts,
   autoimmune diseases such as rheumatoid arthritis, systemic *Lupus erythematosus,* Hashimoto's thyroidis, multiple sclerosis, *Myasthenia gravis,* diabetes type I and uveitis,
   skin manifestations of immunologically-mediated disorders;
   intestinal diseases; and
d) alopecia areata.

The compounds may be administered systemically or topically. For the above indications the appropriate dosage will, of course, vary depending upon, for example, the host, the mode of administration and the nature and severity of the condition being treated. However, in general, satisfactory results are indicated to be obtained systemically at daily dosages of from about 0.15 mg/kg to about 1.5 mg/kg animal body weight. An indicated daily dosage in the larger mammals is in the range from about 0.01 mg to about 100 mg, conveniently administered, for example, in divided doses up to four times a day or in retard form. For topical use satisfactory results are obtained with local administration of a concentration of from about 1% to about 3% by weight of active substance several times daily, e.g. 2 to 5 times daily. Examples of indicated galenical forms are lotions, gels, creams, sprays and solutions.

The compounds of the invention may be administered by any conventional route, in particular enterally, e.g. orally, e.g. in the form of tablets or capsules, or topically, e.g. in the form of lotions, gels, creams, sprays, ophthalmic or nasal solutions or aerosols for local treatment of skin and mucosal membranes, e.g. eye, respiratory tract, vagina, oral and nasal cavity.

Pharmaceutical compositions for e.g. topical application comprising a compound of the invention in free form or where such forms exist in pharmaceutically acceptable salt form in association with at least one pharmaceutical acceptable carrier or diluent may be manufactured in conventional manner by mixing with a pharmaceutically acceptable carrier or diluent. Unit dosage forms contain, for example, from about 0.0025 mg to about 50 mg of active substance.

Topical administration is e.g. to the skin. A further form of topical administration is to the eye, e.g. for the prevention or treatment of immune-mediated conditions of the eye, such as: auto-immune diseases, e.g. uveitis, keratoplasty and chronic keratitis; allergic conditions, e.g. vernal conjunctivitis; inflammatory conditions and corneal transplants; and glaucoma; by the topical administration to the eye surface of a compound of the invention in free form or where such forms exist in pharmaceutically acceptable salt form, in a pharmaceutically acceptable ophthalmic vehicle.

The ophthalmic vehicle is such that the compound is maintained in contact with the ocular surface for a sufficient time period to allow the compound to penetrate the corneal and internal regions of the eye, e.g. the anterior chamber, posterior chamber, vitreous body, aqueous humor, vitreous humor, cornea, iris/cilary, lens, choroid/retina and sclera. The pharmaceutically acceptable ophthalmic vehicle may be e.g. an ointment, vegetable oil, or an encapsulating material.

Whilst the antiinflamatory and immunosuppressant and antiproliferative activity is the main activity of the compounds of the invention they also possess some degree of activity in increasing sensitivity to, or in increasing the efficacy of, chemotherapeutic drug therapy. This activity may e.g. be determined according to the test methods described in EP 360760.

The compounds of the invention are therefore indicated for use in reversing chemotherapeutic drug resistance of varying types, e.g. acquired or innate, or in increasing sensitivity to administered drug therapy, e.g. as a means of reducing regular chemotherapeutic dosage levels, for example in the case of anti-neoplastic or cytostatic drug therapy, as a means of decreasing overall drug toxicity and, more especially, as a means of reversing or reducing resistance, including both inherent and acquired resistance, to chemotherapy.

The invention thus also concerns the use of a compound of the invention in free form or where such forms exist in pharmaceutically acceptable salt form as a pharmaceutical; a such compound of the invention for use as a pharmaceutical; the use of a such compound of the invention for the preparation of a medicament for the prevention or treatment of an inflammatory condition or of a condition requiring immunosuppression; a process for the preparation of a pharmaceutical composition which comprises mixing a such compound of the invention together with at least one pharmaceutically acceptable carrier or diluent; and a method of prevention or treatment of inflammatory conditions and of conditions requiring immunosuppression, comprising administering a therapeutically effective amount of a such compound of the invention to a subject in need of such treatment.

The compounds of the invention may be administered as sole active agent or, conveniently, in combination or association with one or more further pharmaceutically active and compatible agents, e.g. macrolactam macrolides, preferably ascomycin derivatives such as ascomycin itself or ASM.

The invention thus also concerns pharmaceutical compositions comprising a compound of the invention in free form or, where such forms exist, in pharmaceutically acceptable salt form, together with at least one pharmaceutically acceptable carrier or diluent, optionally in combination or association with one or more further pharmaceutically active and compatible agents, e.g. macrolactam macrolides, preferably ascomycin derivatives such as ascomycin itself or ASM. The compound of the invention may be present in such combination or association in widely varying amounts, e.g. from about 99% to about 1% or from about 90% to about 10% generally or, when it is in combination or association with a macrolactam macrolide, preferably with an ascomycin derivative, especially ascomycin itself or ASM, particularly ASM, in view of the similar pharmacological profiles, from about 99.99% to about 0.01%, e.g. about 99.9% to about 0.1%, or from about 95% to about 5%, by weight of respective active agents.

Suitable ascomycin derivatives are e.g. as described in EP 184162, EP 315978, EP 323042, EP 423714, EP 427680, EP 465426, EP 474126, WO 91/13889, WO 91/19495, EP 484936, EP 523088, EP 532089, EP 569337, EP 626385, WO 93/5059 and WO 97/8182;

in particular:

ascomycin itself;
tacrolimus (FK506; Prograf®);
imidazolylmethoxyascomycin (WO 97/8182 in Example 1 and as compound of formula I);
32-O-(1-hydroxyethylindol-5-yl)ascomycin (L-732531) (*Transplantation* 65 [1998] 10–18, 18–26, on page 11, FIG. 1; and
(32-desoxy,32-epi-N1-tetrazolyl)ascomycin (ABT-281) (*J.Invest.Dermatol.* 12 [1999] 729–738, on page 730, FIG. 1);

preferably:

{1R,5Z,9S,12S-[1E-(1R,3R,4R)],13R,14S,17R,18E,21S, 23S,24S,25S,27R}-17-ethyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-5,18-diene-2,3,10,16-tetrone (Example 8 in EP 626385);
{1E-(1R,3R,4R)]1R,4S,5R,6S,9R, 10E,13S,15S,16R,17S, 19S,20S}-9-ethyl-16,20-trihydroxy-4-[2-(4-hydroxy-3-methoxycyclohexyl)-1-methylvinyl]-15,17-dimethoxy-5,11,13,19-tetramethyl-3-oxa-22-azatricyclo[18.6.1.0$^{1,22}$] heptacos-10-ene-2,8,21,27-tetrone (Examples 6d and 71 in EP 569337); and especially:

pimecrolimus (ASM) (Example 66a in EP 427680; 33-epichloro,33-desoxyascomycin).

What is claimed is:
1. A compound of formula I

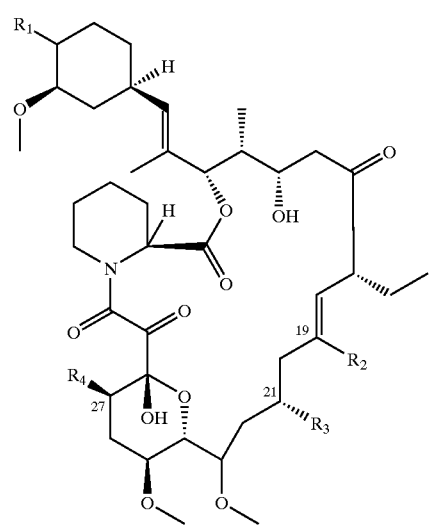

wherein either
  $R_1$ is hydroxy in the β-configuration; and
  $R_2$ is methyl and
  one of $R_3$ and $R_4$ is ethyl and the other is methyl; or
  $R_1$ is chloro in the α-configuration; and
  one of $R_2$, $R_3$ and $R_4$ is ethyl and the others are methyl;
in free form or, where such forms exist, in salt form.

2. A process for the preparation of a compound according to claim 1, which comprises
  a) for the preparation of the compounds of formula I as defined in claim 1 wherein $R_1$ is hydroxy in the β-configuration, cultivating an appropriate microorganism and isolating from the resultant culture medium the corresponding compounds of formula I wherein $R_1$ is hydroxy in the β-configuration; or
  b) for the preparation of the compounds of formula I as defined in claim 1 wherein $R_1$ is chloro in the α-configuration, replacing under epimerization hydroxy with chloro in a corresponding compound of formula I wherein $R_1$ is hydroxy in the β-configuration, and recovering the resultant compound in free form or, where such forms exist, in salt form.

3. A pharmaceutical composition comprising a compound as defined in claim 1 in free form or, where such forms exist, in pharmaceutically acceptable salt form, together with at least one pharmaceutically acceptable carrier or diluent.

4. A composition according to claim 3 wherein the compound is in combination or association with a further pharmaceutically active and compatible agent.

5. A composition according to claim 4 wherein the compound is in combination or association with ASM.

6. A process for the preparation of a pharmaceutical composition according to claim 3 comprising mixing the compound with at least one pharmaceutically acceptable carrier or diluent.

7. A method of prevention or treatment of an inflammatory condition or of a condition requiring immunosuppression, comprising administering to a subject in need of such treatment a therapeutically effective amount of a compound as defined in claim 1 in free form or, where such forms exist, in pharmaceutically acceptable salt form.

* * * * *

UNITED STATES PATENT AND TRADEMARK OFFICE
CERTIFICATE OF CORRECTION

PATENT NO. : 6,706,727 B1
DATED : March 16, 2004
INVENTOR(S) : Fleissner et al.

It is certified that error appears in the above-identified patent and that said Letters Patent is hereby corrected as shown below:

Title page,
Item [30], Foreign Application Priority Data, should be inserted and should read as follows:
      -- May 22, 2000    (GB) ......................... 0012383 --.
Item [57], ABSTRACT,
The chemical formula immediately below the words "The composition of formula I" should read as follows:

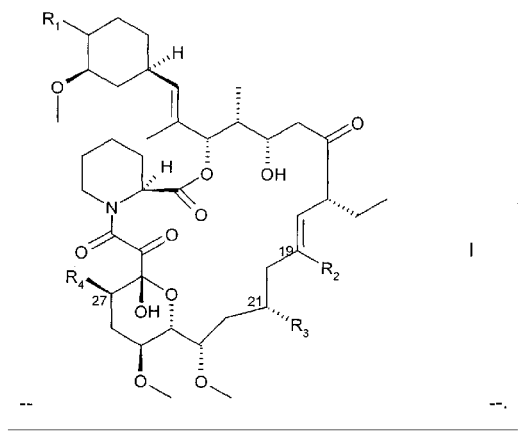

Signed and Sealed this

Twenty-seventh Day of July, 2004

JON W. DUDAS
*Acting Director of the United States Patent and Trademark Office*